United States Patent [19]

Higer et al.

[11] Patent Number: 4,877,021
[45] Date of Patent: Oct. 31, 1989

[54] EMERGENCY AIRWAY SURGICAL DEVICE

[76] Inventors: Gary Higer, 14000 Peach Grove, Sherman Oaks, Calif. 91423; Michael L. Mintz, 141 Kush La., Corpus Christi, Tex. 78404

[21] Appl. No.: 39,620

[22] Filed: Apr. 16, 1987

Related U.S. Application Data

[63] Continuation-in-part of Ser. No. 733,961, May 14, 1985, abandoned.

[51] Int. Cl.⁴ ............................................. A61M 11/00
[52] U.S. Cl. .......................... 128/200.76; 128/207.14; 128/207.17
[58] Field of Search ...................... 128/200.24, 200.26, 128/207.14, 204.15, 305, 305.1, 305.3, 329 R, 341, 345, 348.1, 3, 10, 11, 12; 604/164, 171

[56] References Cited

U.S. PATENT DOCUMENTS

| | | | |
|---|---|---|---|
| 241,036 | 5/1881 | Lyman | 128/305.3 |
| 2,840,082 | 6/1988 | Salvatore | 128/305.3 |
| 3,643,649 | 2/1972 | Amato | 128/305 |
| 3,688,773 | 9/1972 | Weiss | 128/305.3 |
| 3,759,263 | 4/1973 | Taylor | 128/305.3 |
| 3,791,386 | 2/1974 | McDonald | 128/305 |
| 3,817,280 | 6/1974 | Weiss et al. | 128/305 |
| 3,906,956 | 9/1975 | Gilbert | 128/305.3 |
| 3,916,963 | 11/1975 | Pozzi | 128/305.3 |
| 3,991,765 | 11/1986 | Cohen | 128/305 |
| 4,003,381 | 1/1977 | Gilbert | 128/305.3 |
| 4,182,337 | 1/1980 | Nickson | 128/305.3 |
| 4,291,690 | 9/1981 | Jessen | 128/200.26 |
| 4,559,041 | 12/1985 | Razi | 128/305 |
| 4,617,929 | 10/1986 | Gill | 128/305.3 |
| 4,716,901 | 1/1988 | Jackson et al. | 129/305.3 |

Primary Examiner—Max Hindenburg
Assistant Examiner—K. M. Reichle
Attorney, Agent, or Firm—Blakely, Sokoloff, Taylor & Zafman

[57] ABSTRACT

A self contained, emergency airway surgical device is disclosed having a cutting device with a cannula disposed therein. The cutting device has a pair of pivotally attached arms forming a channel therein for containing the cannula with horizontal blades at the end of the arms. The cannula has a blunt downward facing surface on the posterior portion for engaging the posterior lumen of the trachea. A centering rod is slidably coupled to the cannula and is adapted to engage the anterior surface of the lumen of the trachea while the posterior blunt surface of the cannula engages the posterior surface of the lumen thereof to secure the cannula in position therein. The cannula is adapted to receive a tracheal tube for positive ventilation of the lungs.

16 Claims, 3 Drawing Sheets

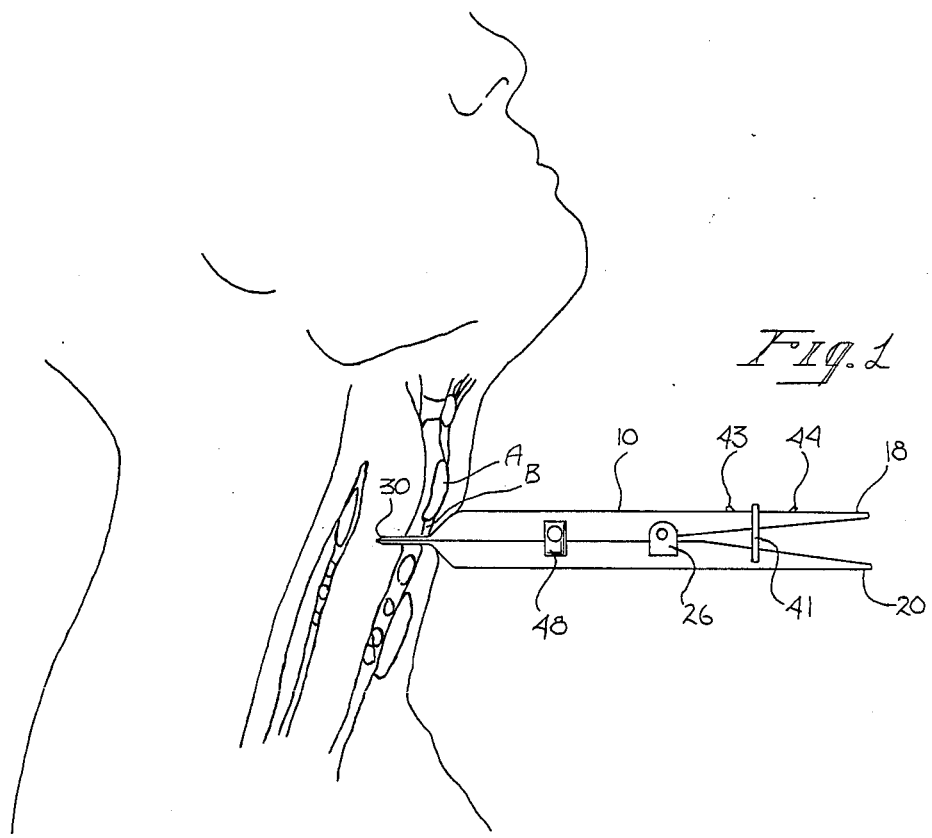
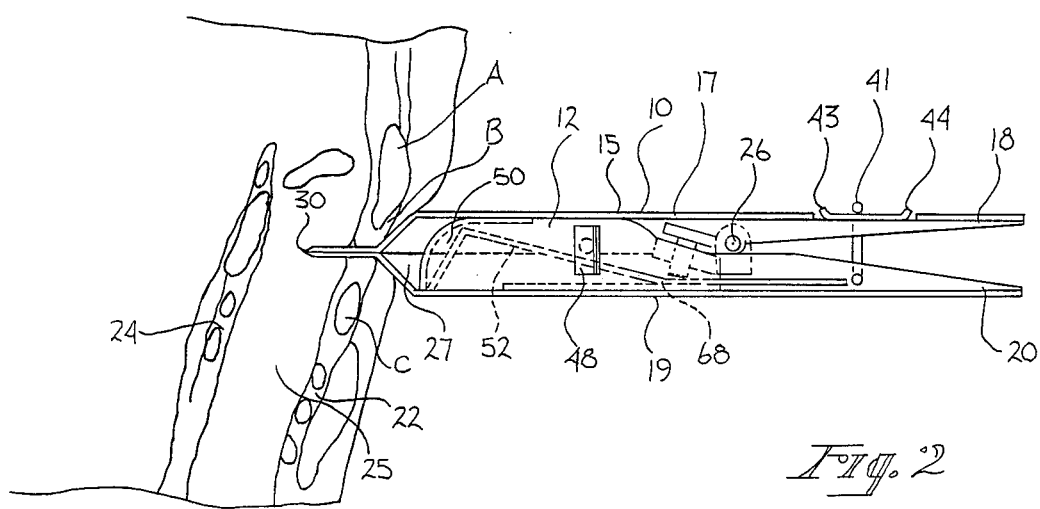

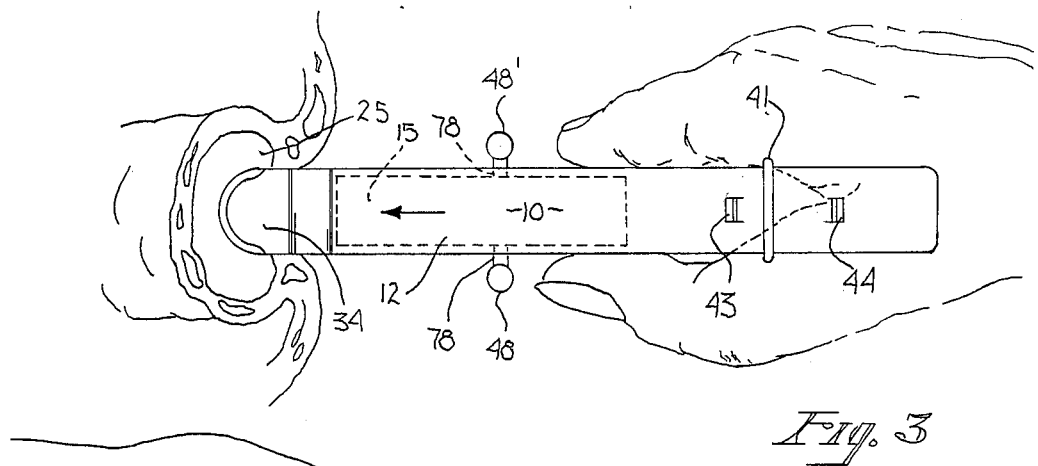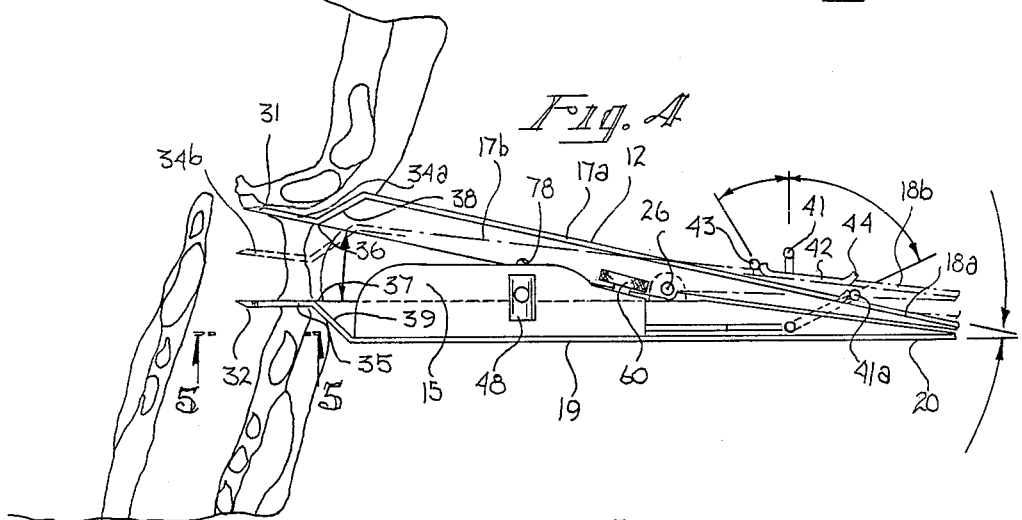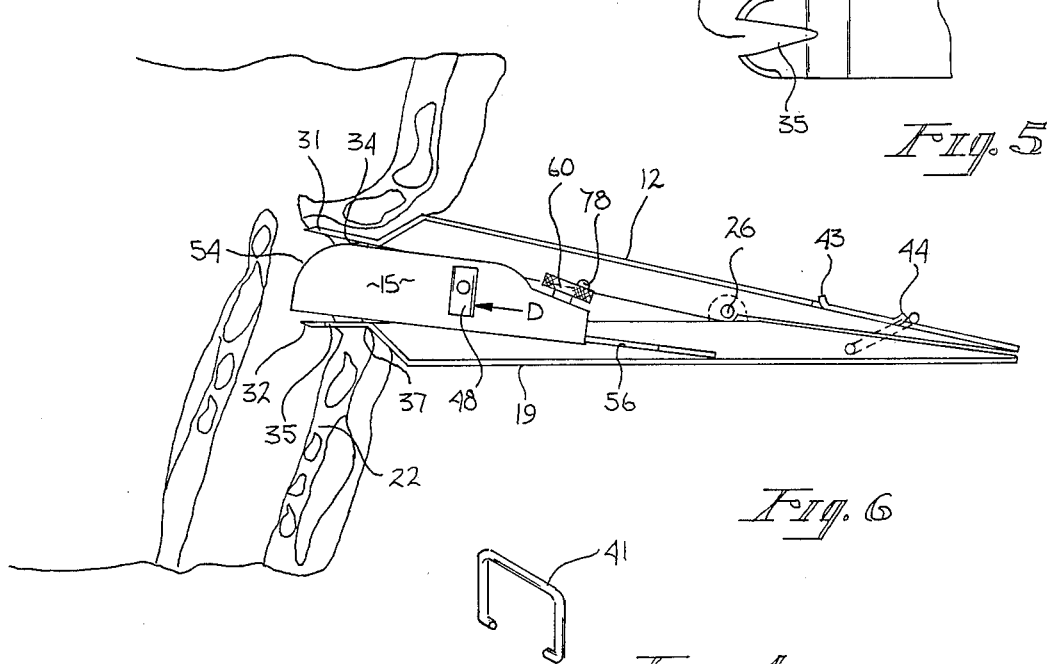

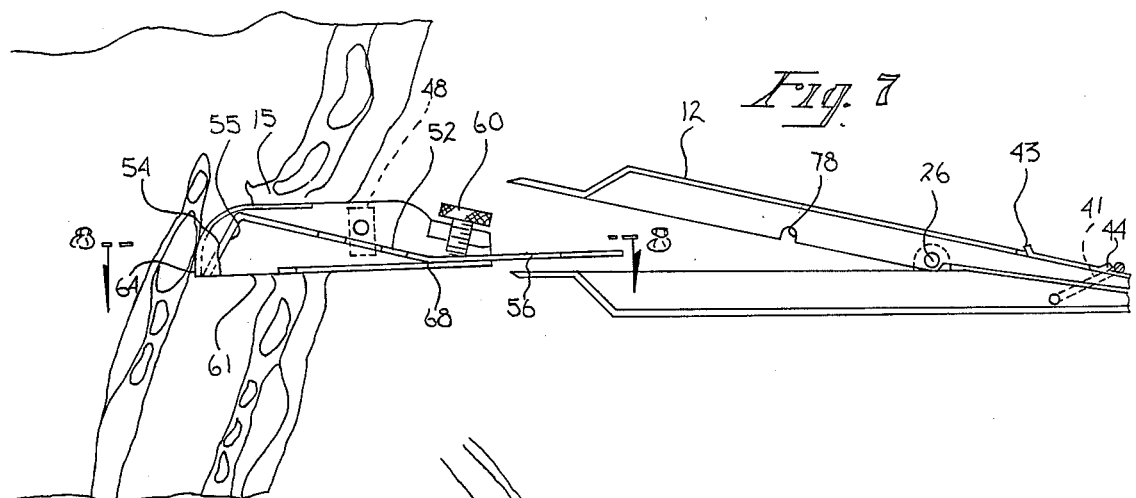
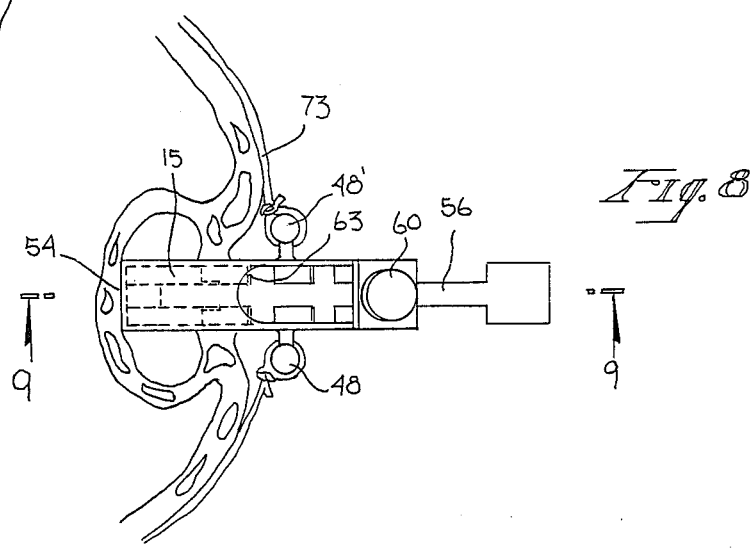
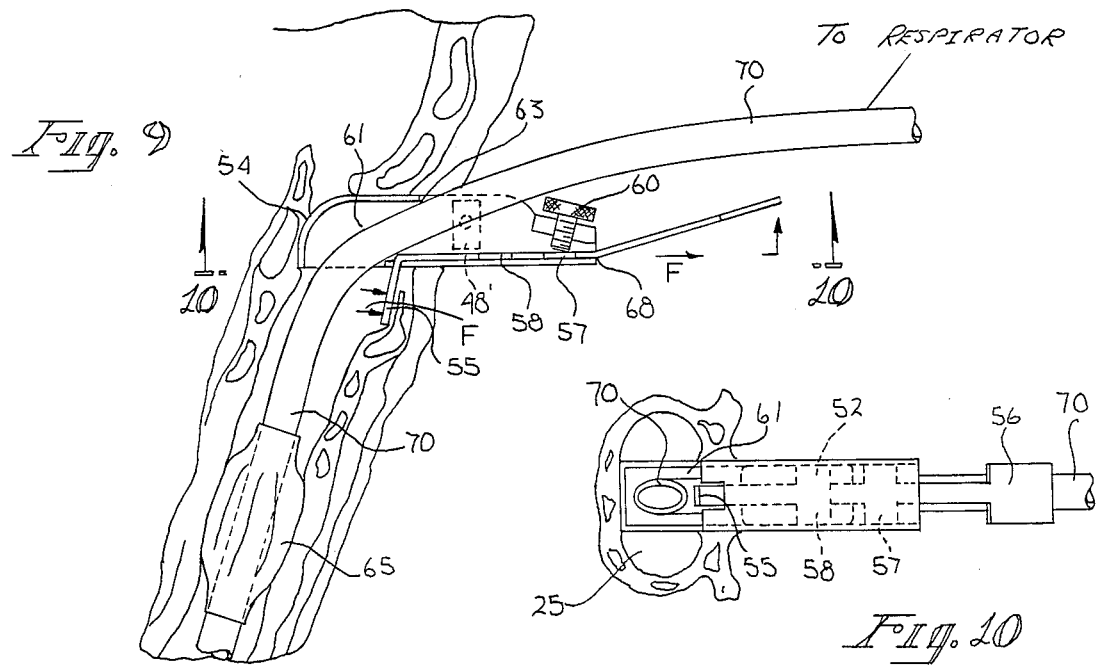
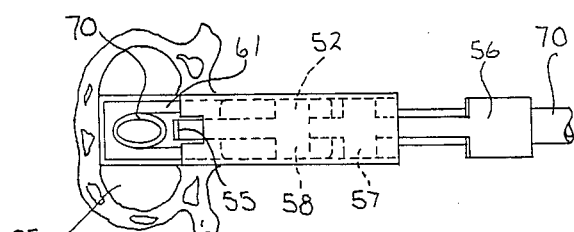

4,877,021

EMERGENCY AIRWAY SURGICAL DEVICE

FIELD OF THE INVENTION

This application is a continuation in part of U.S. application Ser. No. 733,961, filed on May 14, 1985 now abandoned.

This invention relates to emergency cricothyrotomy devices and, more particularly, to trocars and cannulae enabling medical and paramedical personnel to safely perform emergency airway operations by means of a cricothyrotomy.

BACKGROUND OF THE INVENTION

Acute respiratory distress is a life threatening situation for which time is a critical factor in the determination of whether an affected patient lives or dies. In such a situation, a patient may be unable to breath for a variety of reasons, including airway obstruction due to the lodging of a foreign object in the air passage, or the swelling of the tongue or other tissue thereby blocking the air passage to the lungs. No matter what the cause, the result of such condition is that a patient is unable to adequately maintain a satisfactory level of voluntary pulmonary ventilation. In extreme cases where air flow is completely blocked, the patient will die in a matter of 3 to 5 minutes. Such cases frequently occur in restaurants, homes, accident sites and battlefields. As a rule, such places are not likely to be staffed with trained physicians or surgeons, and even if one is present, the means at hand will not usually be adequate to perform a successful tracheotomy, as explained below.

Tracheotomy procedures are well known in the art. A tracheotomy is a surgical procedure used to admit air into the lungs when the normal breathing passage is obstructed, or otherwise ceases to function properly. Briefly stated, a tracheotomy usually involves making an incision through the skin of the neck below the level of the voice box, followed by careful manipulation of the thyroid gland and several large blood vessels to expose the trachea. Thereafter, a small surgical opening is made in the trachea and a specially adapted endotracheal tube is inserted therethrough to maintain the opening and provide an airway. A tracheotomy is the surgical procedure of choice when an auxiliary airway is to be maintained for an extended period of time. However, it is a delicate operation requiring the skill and knowledge of a surgeon and the facilities of a hospital operating room.

When the time and equipment are not available to perform a regular tracheotomy procedure, emergency cricothyroid stab procedures also known as cricothyrotomies have been developed for use by professionals as well as others. The emergency cricothyroid stab procedure involves first identifying the location of the cricothyroid membrane by palpating the thyroid and cricothyroid cartilages. The cricothyroid membrane lies in the area beneath the adams apple and the next lower cartilage ring, which is the cricothyroid cartilage. After the cricothyroid membrane is identified, a rapid incision is made through the skin with any available pointed instrument, and the pointed instrument is rotated 90° around its opening to maintain an airway.

The cricothyroid stab procedure is often performed under emergency conditions where trained surgeons are generally not available. Thus, paramedics, nurses, ambulance and rescue personnel and the like may be confronted with such situations. Therefore, it is important that a cricothyrotomy instrument be available that is simple, quick, easy to use, and readily available for performing the procedure without requiring an extensive amount of surgical skill or training. Such operations have been performed using various devices including scalpels or other cutting blades, curved tracheal cannulae, a multiplicity of large diameter needles, expandable conical punches and tapered trocars having straight or curved fenestrative tubes, as well as simply incising the area and retracting the wound margins and adjacent cartilage by the insertion of small diameter tubes in the incision.

Prior art devices used for surgically gaining access to a patient's trachea generally comprise a standard configuration. The most widely used instruments comprise an arcuate hollow tube which is used in conjunction with an arcuate trocar instrument extendable therethrough, wherein the trocar is used to make the incision. Various types of such instruments are shown in Pozzi U.S. Pat. No. 3,916,903, Gilbert U.S. Pat. No. 3,906,956, Weiss U.S. Pat. No. 3,688,773 and Jessen U.S. Pat. No. 4,291,690. Another prior art device is a cricothyroidotomy needle which is inserted through the cricothyroid membrane. This is technically not a tracheotomy instrument but nevertheless establishes an air passageway into the trachea.

The use of the foregoing equipment is unsuitable for many reasons. For one reason, it is very difficult to insert a blade in the proper location while a patient exhibits usually frantic behavior. Also, none of the prior art devices comprise a means for maintaining the airway open. Moreover, the depth of penetration of the cutting device through the cricothyroid membrane is difficult to ascertain so that there is a risk of puncturing the rear of the trachea thereby causing unnecessary damage thereto.

In addition, the foregoing prior art devices are all deficient in that they do not maximize the size of the aperture to permit a large tube to enter the airway relative to the diameter of the tracheal lumen. Further, the prior art devices are generally not fixed in position so that movement of a device in a posterior direction may result in impingement thereof against the posterior tracheal wall thereby blocking the air passage and causing irritation of the area which may result in post operative infection. Moreover, the prior art devices are not particularly compact and simple to use. Further, such prior art devices are not provided with a means for securing such devices in position for extended periods of time.

SUMMARY OF THE INVENTION

The present invention is not subject to the aforementioned limitations in function and design. The invented device is designed to remain securely centered in the anterior-posterior and transverse planes within the trachea and to maximize the aperture within the trachea lumen available for ventilatory support. Moreover, the device is a simple two piece surgical instrument providing all of the necessary components for a safe, quick, accurate and successful cricothyrotomy by a person with minimal medical training. The device is, of course, also useful for those with extensive medical training, as well.

The invented cricothyrotomy instrument consists of two parts, a cutting member and a cannula removably disposed within the cutting member. The cutting member comprises two arms having a sharpened edge at the end thereof and formed with a generally rectangular or rounded channel therein to house the cannula. The arms of the cutting member are pivotally connected to have a scissor-like operation so that closing the arms together at the digtal end opens the blades at the proximal end. The sharpened edges or blades of the cutting member are flattened and the inferior blade is slightly shorter than the superior blade and is notched so that the blades do not entirely overlap each other, so that immediate airway passage is provided upon insertion of the cutting member blades into the trachea. The cutting means also comprises a locking means to hold the blades open thereby separating the cricothyroid cartilage so that the cannula can be inserted therein. A hole is provided in each side of the cutting member so that a handle on the cannula extends outside the cutting member for convenient access and handling thereof.

The cannula has a downward curving proximal end for abutting the posterior surface of the lumen of the trachea and a slidably engaging generally L-shaped centering member. The centering member is adapted to be substantially retracted within the cannula so that the cannula can fit within the cutting member. A channel is formed in the top and bottom of the cannula to provide ventilation therethrough, and, if desired, so that a tracheal tube can be inserted therethrough. The centering member can be moved and locked in a downward position so that it is disposed against the anterior surface of the lumen of the trachea to hold the cannula in place and provide an opening through which a tracheal tube may be disposed. Thus, when the device is properly installed in the trachea the posterior portion abuts the posterior surface of the lumen of the trachea thereby securing the device in position in the trachea and preventing dislodging of the same.

BRIEF DESCRIPTION OF THE DRAWINGS

FIG. 1 illustrates a side view of the invented device with the blades of the cutting member penetrating through the cricothyroid membrane of a patient.

FIG. 2 is an enlarged sectional view of the cutting member with the cannula therein (partially shown in ghost lines).

FIG. 3 is an enlarged superior plan view of the invented device penetrating the trachea with the cannula and a portion of a hand shown in ghost lines.

FIG. 4 is an enlarged sectional view of the cutting means with the cannula therein showing the cutting means in partial (shown in ghost lines) open position and in full open position.

FIG. 4a is an enlarged view of the locking means.

FIG. 5 illustrates a plan view of the lower blade of the invented device taken through lines 5—5 of FIG. 4.

FIG. 6 is an enlarged sectional view of the cutting means with the cannula therein illustrating the insertion of the cannula into the trachea.

FIG. 7 is an enlarged partially sectional view of the cannula and cutting means illustrating the removal of the blades and the full insertion of the cannula disposed within the trachea.

FIG. 8 is a superior plan sectional view of the cannula disposed in the trachea and taken through lines 8—8 of FIG. 7.

FIG. 9 is a sectional view of the cannula taken through lines 9—9 of FIG. 8 with a respirator tube disposed therein.

FIG. 10 is an inferior plan view of the cannula disposed in the trachea and taken through lines 10—10 of FIG. 9.

DETAILED DESCRIPTION

With reference to FIGS. 1-2, the laryngeal-tracheal region of the anatomic structure for a patient is shown. The thyroid cartilage A is directly above the cricothyroid membrane B and the cricothyroid cartilage C. The anterior surface of the tracheal lumen 22 and posterior surface of the tracheal lumen 24 are also shown.

The surgical instrument of the present invention is shown generally as 10 and comprises a cricothyrotomy tube member or cannula 12 disposed within a cutting member 15, as shown for example in FIG. 2. The cutting member 15 comprises an upper or superior arm 17 and lower or inferior arm 19 attached at a pivot means or hinge 26. A blade 30 is disposed on the end of said cutting member 15. The blade 30 is sharp and flattened so that a side-to-side movement thereof against tissue, particularly the skin and cricothyroid membrane of a patient produces the desired cutting effect.

As shown in FIG. 3, which is a superior plan view of the invented device inserted in the trachea 25, the superior blade 34 has a rounded profile. As shown in FIG. 5, the inferior blade 35 has a notch 36 disposed therein to permit air passage therethrough as soon as the blade 30 is inserted into the trachea 25. The superior blade 34 is generally slightly longer than the inferior blade 35. In this configuration, an air passageway is created as soon as the blades cut through the cricothyroid membrane. The notch provides a clear pathway for the air when the blades are closed from the exterior of the cutting member to the interior thereof. Further, when superior blade 34 and inferior blade 35 are closed, they form an integral flat cutting blade 30. When the blades are open, the blades are angled such that the cricothyroid membrane B is retained on the blade and the cutting member 15 is held in position in the opening. This is accomplished because the distance between the posterior ends 31 and 32 of the upper 34 and lower 35 blades is slightly greater than the distance between the anterior ends 36 and 37 of the blades 34 and 35, respectively. Therefore, the pressure of the cricothyroid membrane on the blades forces the blades in a posterior direction P until the membrane is held against flanges 38 and 39. The broad, flat blades 34 and 35 also aid in controlling the bleeding by applying direct pressure on the cut portion of the skin and membrane.

The pivot means 26 is disposed along the length of the cutting member 15 so that squeezing the rear portions 18 and 20 of arms 17 and 19 respectfully will cause blades 34 and 35 to open. In this regard, it should be understood that approximately 40 foot pounds of pressure is required to separate the blades 34 and 35 when disposed within the cricothyroid membrane. Thus, the pivot means 26 should be disposed so that the blades 30 are appropriately leveraged so that pressure on the cutting member handles 18 and 20 will enable the blades 30 to open and overcome the pressure thereon.

In order to secure the blades 30 in an open position after insertion into the cricothyroid membrane, a locking means is provided. Although any type of locking means can be used, in the preferred embodiment particularly shown in FIGS. 4 and 4a, the locking means comprises a bar 41 and a latch 42 having detents 43 and 44. Detents 43 and 44 should preferably be asymmetrically disposed with respect to bar 41 so that the blades 30 can be opened varying amounts pending upon the desired opening size. As specifically shown in FIG. 4, when the bar is in position 41b hooked onto latch 43, the cutting member arm is in position 17b and is disposed in a half-way open position. This position might be used for small children and the like whose cricothyroid membranes are relatively small compared to adults and cannot be stretched as far. When the bar is in position 41a disposed behind latch bar 44, the cutting member 10 is in the fully opened position with the upper arm in position 17a disposed the furthest from lower arm 19. Similarly, upper blade 34 as seen in position 34a is furthermost spaced apart from lower blade 35 when the device is fully opened as when it is used on adults, and blade 34 as seen in position 34b is only half-way opened as when the device is used on children. It is anticipated that when using the present device for children, a smaller cannula member 12 may be used. Although a smaller cutting member 15 may be used with the smaller cannula member 12, it is preferable to have a universally acceptable instrument useful for patients of all sizes, and the disclosed cutting member 15 can generally be used for most patients.

In other embodiments it is anticipated that the locking member can be a ring, screw, or other device which can similarly hold the blades 30 of the invention 10 in an open position of predetermined size.

Now referring to FIGS. 2–9, the cannula 12 will be described. Although the cannula 12 is shown in the drawings with a square profile, any shape will suffice; however, it is preferable that the cannula have a easily visually distinguishable top and bottom to avoid confusion during emergency procedures.

Moreover, the square profile with flat top and bottom surfaces adapted to engage the cricothyroid membrane is more stable when disposed in position, and is less likely to rotate. In this regard, the stability of the instrument in position is important because if a tracheal tube is not inserted into the cannula properly, so that it goes down the trachea without irritating the internal membranes thereof, unnecessary complications of the procedure can develop. As clearly shown in FIG. 2, the cannula 12 is disposed within the channel or cavity 27 formed within the cutting member 15. The channel may be partially or fully enclosed. The cannula 12 comprises a housing 50 and a centering means 52. As can be clearly seen in FIG. 6, the housing 50 has a rounded posterior portion designed to easily slide out between the blades 34 and 35 and to safely engage the posterior surface of the tracheal lumen 24 without causing any substantial injury or irritation thereto. Although the housing 50 is depicted herein having a rounded leading edge 54, any blunted surface will properly function for the instrument to avoid traumatizing the trachea.

On the sides of said housing 50, a handle is disposed to assist the user in removing the cannula 12 from the cutting member 15. In the preferred embodiment, the handle comprises a pair of tabs 48 which may be gripped from the sides to manipulate the cannula 12. These tabs may be cylindrical, looped, circular or any other shape which permits the user to easily push the cannula in position. Preferably circular or loop tabs 48 are provided so that a securing string can be attached to hold the cannula in position as described below.

The tabs 48 extend through holes 78 in cutting member 15 to the outside thereof to allow for simple removal of the cannula 12 from the cutting member 15. However, any configuration, design or positioning of the tabs 48 may be utilized without departing from the spirit and scope of the invention.

A centering means 52 is disposed within and is slidably attached to the housing 50 as shown in FIG. 7, which illustrates a cutaway view of the cannula 12. When the cannula 12 is disposed in the cutting member 15, the centering means 52 is disposed within the cannula 12 in an upward position, as shown in FIG. 7, and which may be compared with FIG. 9, in which the centering means 52 is in a downward position. Centering means 52 aligns with locking means 60 to permit the centering means 52 to be locked in either its upward or downward positions. For purposes of inserting the cannula 12 within the trachea 25, centering means 52 is fully disposed within the housing 50 except for tail 56 which extends out of the housing 50 and which is used to grip and maneuver centering means 52. The centering means 52 is angled at 68 so that it can be held in an up position so as not to interfere with insertion or retraction of the cannula in the trachea. When the centering means 52 is moved out of housing 50 in direction D, the flange 55 moves downward and into position to engage the anterior surface 22 of the lumen of the trachea. The purpose of the initial motion of flange 55 being downward at the furthest posterior position of the centering means is to ensure that the flange 55 can descend into the trachea 25 without the risk of impinging on the cricoid cartilage.

In particular, as shown in FIG. 9, when centering means 52 is moved in direction D with respect to the cannula 12, screw 60 depresses flat middle portion 57 against bottom portion 58 of cannula 12 causing flange 55 to be forced downward. Thus, with the posterior portion 54 of the housing 50 in place against the posterior surface 24 of the lumen of the trachea, flange 55 is disposed against the anterior surface 22 of the lumen of the trachea, and centering means 52 is fixed in position with respect to housing 50, so that the cannula 12 is secured in position.

Once the cannula 12 is secured in position, a tracheal tube can be inserted through the cannula 12 and down into the trachea. As shown in FIG. 8, the housing 50 has an open window 63 disposed therein to permit the free flow or air therethrough. The window 63 permits passage of a tracheal tube 70 therein as shown in FIG. 9. The tracheal tube 70 may be disposed through window 63 of the cannula 12 and down into the trachea 25 to permit adequate mechanical ventilation of the lungs. The internal surface of posterior end 54 of the housing is preferably gradually downwardly sloped to aim the tracheal tube down the trachea 25. Tube 70 may be attached to a respirator system as is well-known in the art for this purpose. As shown in FIG. 9, standard tracheal tubes usually comprise a balloon-like bubble 65 that may be inflated to fill the trachea to block air passage above the end of tube 70 thereby insuring positive ventilation to the lungs.

In use, the device preferably comprises a square profiled cannula 15 with a rounded posterior edge 54 which advances across the trachea 25 to atraumatically contact the posterior surface 24 of the trachea lumen. The inferior surface of the advancing cannula 12 contains a hole 61 to provide initial ventilation to the lungs and to permit free anterior movement of the centering means 52 so that the flange 55 may be advanced to the anterior surface of the tracheal lumen 22.

The device is inserted into the trachea through the cricothyroid membrane. The target area is located by palpating the area to locate the membrane. Using a side-to-side cutting motion, the blades 30 penetrate through the skin and the cricothyroid membrane into the upper airway at the anterior surface 22 of the lumen of the trachea. The blades 30 are opened thereby spreading the cricothyroid membrane to produce an opening in which the cannula 12 will be placed. Once opened, the blades 30 are locked in an open position to perform the next step. The pressure of the blades on the newly cut cricothyroid membrane and skin, limits the amount of bleeding in the area.

The configuration of the square housing 50 with the blunt posterior edge 54 allows atraumatic advancement of the posterior edge 54 of the housing 50 into the trachea 25 to a point where the hole 61 marginally or completely overlies the trachea 25. At this point, the locking means 60 for the centering means 52 is loosened and the flange 55 lying above the posterior edge 64 of the housing 50 moves downward as tail 56 is pulled anteriorly in direction F. In sliding the centering means 52 anteriorly so that angle 68 passes locking means 60, flange 55 enters the trachea 25 and is then advanced to the anterior surface of the tracheal lumen 22. The free movement of centering means 52 and the advancement of the posterior edge 54 of the housing 50 to the posterior surface of the tracheal lumen 24 assures the operator of the device that the airway has been established. The centering means 52 is then locked in place using locking means 60. In addition, the diameter of the lumen available for airway support is maximized once the cannula 12 is secured as aforesaid in the trachea 25, and a tracheal tube 70 may be inserted therein to create a positive pressure source to assist the patient's breathing.

The cannula 12 can be secured in position by the attachment of a cord, thread, adhesive and the like to the tabs 48. In the preferred embodiment, a cord 63 is disposed around the neck of the patient and is attached to the handles 48.

The present invention has been described in its preferred embodiment herein. It will be obvious to one of ordinary skill in the art that the parameters hereof can be modified without departing from the spirit and scope of the present invention.

We claim:

1. A laryngeal-tracheal instrument for permitting pulmonary ventilation of a subject comprising:
   (a) a cutting means for incising a trachea of the subject comprising:
      (i) a housing defining a cavity, said housing divided horizontally to form a pair of horizontally aligned superior and inferior arms, and including pivot means disposed between the arms for pivotally interconnecting said arms to enable scissor-like movement; and
      (ii) a sharpened flattened blade horizontally disposed of the posterior end of each of said arms, said blades forming a unitary horizontal cutting edge when said arms are in a closed relationship; and
   cannula means disposed within said cavity formed by said arms and removable at the posterior end thereof when said arms are in an open relationship, said cannula means comprising:
      (i) a housing having a blunt posterior surface and being of adapted to engage the posterior portion of the trachea of the subject, an inferior surface having an opening in the posterior portion thereof and a superior surface having an opening in the anterior portion thereof, said housing being sized such that when the posterior surface engages the posterior portion of the trachea, the opening in the superior surface is external of the subject; and
      (ii) centering means adjustably disposed within said housing, said centering means comprising a flattened member means and inferiorly angled flange means at the posterior thereof adapted to engage the anterior portion of the trachea, said flattened member means being adapted to move from a first position in which said flange means is disposed substantially within said housing for easy insertion into the trachea to a second position where said flange means extends through said opening in the inferior surface of the housing and engages the anterior portion of the trachea when said posterior surface of the housing engages the posterior portion of the trachea thereby securing said cannula means in position.

2. The instrument of claim 1 wherein said cutting means further comprises latch means for securing said blades in at least one open position.

3. The instrument of claim 2 wherein said latch means is adapted to secure said blades in at least one partially open position and in a fully open position.

4. The instrument of claim 2 wherein said latch means comprises bar means coupled to one of said arms and at least one hook means attached to the other of said arms so that when said bar means is coupled with said hook means, said arms are secured in at least one open position.

5. The instrument of claim 1 wherein the blade on said superior arm is longer than the blade on said inferior arm.

6. The instrument of claim 5 wherein said blade on said inferior arm has a notch therein providing free fluid flow between the outside and the inside of the cutting means when said arms are disposed together in a closed relationship so that an air passageway is established upon penetration of the cutting means into the trachea.

7. The instrument of claim 5 wherein said blades are of such shape and horizontal size so as to substantially reduce bleeding of the subject in the area of an incision made by said blades.

8. The instrument of claim 1 further comprising securing means and said cannula means further comprises a handle means disposed on the exterior thereof, said handle means for receiving the securing means to secure said cannula in the trachea of the subject.

9. The instrument of claim 8 wherein said handle means comprises tab means disposed on opposing sides of said cannula means, said securing means comprises a cord and the cord is adapted to be tied to each of said tab means.

10. The instrument of claim 1 wherein said housing is adapted to receive a tracheal tube through said openings in the inferior and superior surfaces of the housing when said flattening member means is in the second position.

11. The instrument of claim 10 wherein said posterior surface of the housing is curves such that said posterior surface of the housing guides the tracheal tube into the trachea through said opening in the inferior surface of the housing.

12. The instrument of claim 10 wherein said cannula means further comprises locking means for securing said centering means in a predetermined position.

13. The instrument of claim 1 wherein said centering means is slidably coupled to said cannula means.

14. The instrument of claim 13 wherein said centering means further comprises superiorly angled portion means at the anterior end of the flattened member means for manually activating the movement of the flattened member means such that when said superiorly angled portion means is activated, said inferiorly angled flange means moves in an inferior direction.

15. The instrument of claim 1 wherein said inferior and superior surfaces of the housing are substantially flat whereby said cannula means is positionally stable when disposed within the subject.

16. The instrument of claim 15 wherein said cannula means has a square cross-section.

* * * * *